US009539356B2

(12) United States Patent
Eike

(10) Patent No.: US 9,539,356 B2
(45) Date of Patent: Jan. 10, 2017

(54) INLINE AIR TREATMENT DEVICE

(71) Applicant: Mason Edward Eike, Westminster, CO (US)

(72) Inventor: Mason Edward Eike, Westminster, CO (US)

( * ) Notice: Subject to any disclaimer, the term of this patent is extended or adjusted under 35 U.S.C. 154(b) by 0 days.

(21) Appl. No.: 14/705,138

(22) Filed: May 6, 2015

(65) Prior Publication Data
US 2015/0359919 A1 Dec. 17, 2015

Related U.S. Application Data

(60) Provisional application No. 62/011,375, filed on Jun. 12, 2014.

(51) Int. Cl.
*A61L 9/12* (2006.01)
*F24F 3/16* (2006.01)
*A61L 9/013* (2006.01)

(52) U.S. Cl.
CPC ............... *A61L 9/12* (2013.01); *A61L 9/013* (2013.01); *A61L 9/122* (2013.01); *A61L 2209/16* (2013.01); *Y10T 29/49828* (2015.01); *Y10T 137/4891* (2015.04)

(58) Field of Classification Search
CPC ....................................................... A61L 9/22
USPC .......................................................... 422/120
See application file for complete search history.

(56) References Cited

U.S. PATENT DOCUMENTS

| | | |
|---|---|---|
| 2,554,694 A | 5/1951 | Belt |
| 2,940,835 A | 6/1960 | Scofield |
| 3,392,509 A | 7/1968 | Pelosi, Jr. |
| 3,661,323 A | 5/1972 | Farris |
| 4,067,692 A | 1/1978 | Farris |
| 4,603,030 A | 7/1986 | McCarthy |
| 4,612,909 A | 9/1986 | Lee |
| 5,165,603 A | 11/1992 | Hahn |
| 5,240,487 A | 8/1993 | Kung |
| 5,306,207 A | 4/1994 | Courts |
| 5,447,693 A | 9/1995 | Ohta et al. |
| 5,562,407 A | 10/1996 | Cielo |
| 5,690,719 A | 11/1997 | Hodge |
| 5,860,412 A | 1/1999 | Way |
| 5,873,529 A | 2/1999 | Johnson |

(Continued)

*Primary Examiner* — Kevin Joyner
*Assistant Examiner* — Holly Mull
(74) *Attorney, Agent, or Firm* — Marsh Fischmann & Breyfogle LLP; Jonathon A. Szumny

(57) ABSTRACT

An airflow treatment device configured to be installed inline in the ductwork of an air handling system (e.g., HVAC system) in a manner that is substantially free of obstructing the airflow through the ductwork or requiring any supplemental power to treat the airflow passing by the treatment device. The disclosed airflow treatment device can also be maintained substantially free of any interruptions, disassembly or downtime to the air handling system after initial inline installation of the disclosed device. In one arrangement, the airflow treatment device is capable of accepting a threaded odor neutralizer container at its base. Ductwork need only be disassembled once to attach the disclosed device inline in the airflow path of the ductwork. When the odor neutralizing agent needs replenished, the container can be detached from the device, replenished, and reattached to the device free of disruption to the air flow of the air handling system.

10 Claims, 14 Drawing Sheets

(56) References Cited

U.S. PATENT DOCUMENTS

| | | |
|---|---|---|
| 5,924,597 A | 7/1999 | Lynn |
| 5,931,014 A | 8/1999 | Cole |
| 5,957,771 A | 9/1999 | Baek |
| 6,032,930 A | 3/2000 | Calino |
| 6,076,748 A | 6/2000 | Resch et al. |
| 6,602,463 B1 | 8/2003 | Ortner |
| 6,935,387 B1 | 8/2005 | Blubaugh |
| 7,740,686 B2 | 6/2010 | Metteer |
| 7,856,675 B1 | 12/2010 | Couturier et al. |
| 8,251,299 B1 | 8/2012 | Irvin |
| 8,500,890 B2 | 8/2013 | Sluis |
| 2003/0150222 A1 | 8/2003 | Mirowsky et al. |
| 2004/0073998 A1 | 4/2004 | Zahavi |
| 2005/0039835 A1 | 2/2005 | Yamane |
| 2005/0066818 A1* | 3/2005 | Kim .................. A61L 9/122 96/222 |
| 2006/0110281 A1* | 5/2006 | Smith .................. A61L 9/037 422/5 |
| 2006/0288871 A1 | 12/2006 | Crapser et al. |
| 2007/0089387 A1 | 4/2007 | Ramos |
| 2007/0227362 A1 | 10/2007 | Parker |
| 2008/0063558 A1 | 3/2008 | Coleman |
| 2008/0169359 A1* | 7/2008 | Carrubba .............. E03C 1/046 239/310 |
| 2010/0018398 A1 | 1/2010 | Krell et al. |
| 2010/0264232 A1* | 10/2010 | Gruenbacher .......... A61L 9/04 239/6 |
| 2011/0138863 A1 | 6/2011 | Kim et al. |
| 2013/0146783 A1 | 6/2013 | Boodaghians et al. |
| 2013/0232931 A1 | 9/2013 | Malcolm |
| 2014/0097266 A1 | 4/2014 | Habbel |

* cited by examiner ically securable or releasably receivable within the third opening of the one-piece body; wherein the one-piece body is configured to be installed inline in existing ductwork of an air handling system to limit disturbance to airflow through the ductwork.

INLINE AIR TREATMENT DEVICE

CROSS REFERENCE TO RELATED APPLICATION

This application claims priority to U.S. Patent App. No. 62/011,375, entitled "INLINE APPARATUS CAPABLE OF ACCEPTING A THREADED CONNECTION AT ITS BASE," and filed on Jun. 12, 2014, the entire contents of which are incorporated herein in their entirety as if set forth in full.

BACKGROUND OF THE INVENTION

1. Field of the Invention

This invention relates to the field of heating, ventilating and air conditioning (HVAC) systems and, more particularly, to devices that treat airflow through the ductwork, hoses or the like of HVAC systems.

2. Description of Related Art

It is common to employ one or more devices in homes, buildings, and other enclosed spaces to treat the air being inhaled by inhabitants in various manners. As one example, various types of odor management (e.g., neutralizing or elimination) systems have been utilized in which an air flow is moved past a product which may be vaporized, either by evaporation or sublimation, in order to distribute the vaporized product throughout the surrounding environment to neutralize, treat, purify and/or freshen the air and/or the like. For instance, some odor management systems are installed "inline" in the ductwork or hosing of an HVAC system so that activation of the HVAC system (e.g., including triggering of the blower fan in the HVAC system) simultaneously initiates activation of the odor neutralizing or elimination system.

SUMMARY OF THE INVENTION

Existing inline ductwork odor management systems are generally expensive to install, are prone to maintenance that requires expensive replacement parts, and inefficiently treat the air leading to sub-optimal levels of odor neutralization and/or elimination. For instance, some existing odor management devices (e.g., including odor neutralizing agents) are physically placed across the airflow path of the ductwork which necessarily obstructs the airflow and increases the power demands of the blowing componentry. Oftentimes, disassembly of these devices is required which adds wear to system components, adds weight if being suspended in the air for mounting purposes and can result in undesirable air being present where the disassembly occurs. Physical obstruction of the airflow and/or sagging of the ductwork due to the suspended componentry ultimately leads to inefficient airflow, unneeded recurring labor, and increased maintenance costs.

As another example, some odor management devices require supplemental electrical components and power to operate (e.g., independent of that of an HVAC system), such as electrically powered dispensing agent. However, some of these agents can break down causing particles to travel throughout an HVAC system leading to an increased risk of damage to downstream ventilation components as well as fire hazards. Furthermore, supplement power requirements increase overall energy consumption by the home, building, etc.

In this regard, disclosed herein is an airflow treatment device configured to be installed inline in the ductwork of an air handling system (e.g., HVAC system) in a manner that is substantially free of obstructing the airflow through the ductwork or requiring any supplemental power to treat the airflow passing by the treatment device. The disclosed airflow treatment device can also be maintained substantially free of any interruptions, disassembly or downtime to the air handling system after initial inline installation of the disclosed device. Broadly, the disclosed airflow treatment device includes an airflow passageway including first and second opposite openings that may be installed inline in the existing ductwork of an air handling system (e.g., vertically, horizontally, etc.) to treat air entering a building or home or exiting a building or home as well as an air treatment passageway that provides access to the airflow passageway.

As just one example, an existing duct of an air handling system may be appropriately separated (e.g., split, cut, etc.) into first and second duct members having respective open ends. The respective open ends of the first and second duct members may then be appropriately secured (e.g., with hose clamps or the like) over the first and second openings of the airflow treatment device so that the airflow passageway extends through the first duct member, the first and second openings of the device, and the second duct member. In one arrangement, the airflow treatment device may be appropriately hung from or otherwise secured to a fixed member (e.g., structural member of the house or building, such as a joist, etc.) at a point above the first and second duct members to limit or otherwise reduce the load placed on the ductwork by the airflow treatment device. As just one example, the airflow treatment device may have a first connector member (e.g., hole, hook, opening, etc.) that is configured to connect with a corresponding second connector member (e.g., hook, hole, etc.) on a joist or other fixed member of the house or building.

The airflow treatment device also includes an air treatment passageway including a first opening over which an air treatment container (e.g., jar, bottle, etc.) may be appropriately releasably secured and an opposite second opening that intersects or otherwise feeds into the airflow passageway. For instance, the airflow treatment device may have a threaded member adjacent or about the first opening of the air treatment passageway onto which an opening of the air treatment container may be threaded. The air treatment container may have any appropriate air treatment or odor neutralizing substance or agent therein (e.g., including one or more essential oils, etc.) to appropriately treat the airflow through the airflow passageway. When the air treatment substance needs to be replenished, the air treatment container may be appropriately disconnected (e.g., unscrewed) from the airflow treatment device and the air treatment substance may be replenished before re-securing the air treatment container to the airflow treatment device. The air treatment container may be secured to and removed from the airflow treatment device free of disconnecting the airflow treatment device from the first and second duct members or otherwise disrupting the air handling system. In one embodiment, an adapter or coupling member may be used to interconnect the air treatment container to the airflow treatment device, such as when the air treatment container is not configured to be directly interconnectable to the airflow treatment device.

In one aspect, a kit for use in treating airflow in ductwork includes a one-piece body having first and second openings that define an airflow passageway therebetween and a third opening between the first and second openings that provides access to the airflow passageway; and an air treatment container that is one of releaseably securable or releasably secured to the body over the third opening, where the air treatment container includes an air treatment substance therein to treat airflow through the airflow passageway.

For instance, the body may include a first threaded member adjacent the third opening, where the air treatment container includes a second threaded member that is threadably engageable with the first threaded member to releasably secure the air treatment container to the body. In one arrangement, a screening element may be disposed over the third opening to limit particulates or the like of the odor or air treatment substance from entering the airflow passageway.

In another aspect, a kit for use in treating airflow in ductwork includes an airflow treatment device including a first body having a first wall that defines an airflow passageway and a second body having a second wall that defines a first portion of an air treatment passageway that intersects the airflow passageway. The first wall includes first and second opposite open ends, where the airflow passageway extends between the first and second opposite open ends of the first wall. The second wall includes first and second opposite open ends, where the first portion of the air treatment passageway extends between the first and second opposite open ends of the second wall, and where the first open end of the second wall is disposed outside of the airflow passageway. The disclosed kit also includes an air treatment container that is one of releaseably securable or releasably secured to the first open end of the second wall. The air treatment container includes a third body having a third wall that defines a second portion of the air treatment passageway that feeds into the first portion of the air treatment passageway, where the third wall includes a closed first end and an opposite open second end, and where the second portion of the air treatment passageway extends between the closed first end and the opposite open second end of the third wall.

In one arrangement, the device includes a first releasable interconnection apparatus and the airflow treatment container includes a second releasable interconnection apparatus that is complimentary to the first releasable interconnection apparatus. For instance, the first releasable interconnection apparatus may be a first set of threads and the second releasable interconnection apparatus may be a second set of threads that is threadably engageable with the first set of threads. In one arrangement, the first releasable interconnection apparatus may be disposed on one of the inside or the outside of the second wall and the second releasable interconnection apparatus may be disposed on the other of the inside or the outside of the third wall.

In one arrangement, a system includes the kit, an open end of a first duct secured over the first open end of the first body, and an open end of a second duct secured over the second open end of the first body, where the airflow passageway is defined through the first duct, the first body, and the second duct.

In one arrangement, a method includes securing an open end of a first duct member over the first open end of the first body of the kit and securing an open end of a second duct member over the second open end of the first body of the kit, wherein the airflow passageway is defined through the first duct, the first body, and the second duct.

In addition to the exemplary aspects and embodiments described above, further aspects and embodiments will become apparent by reference to the drawings and by study of the following descriptions.

DESCRIPTION OF THE INVENTION

Figure 1:
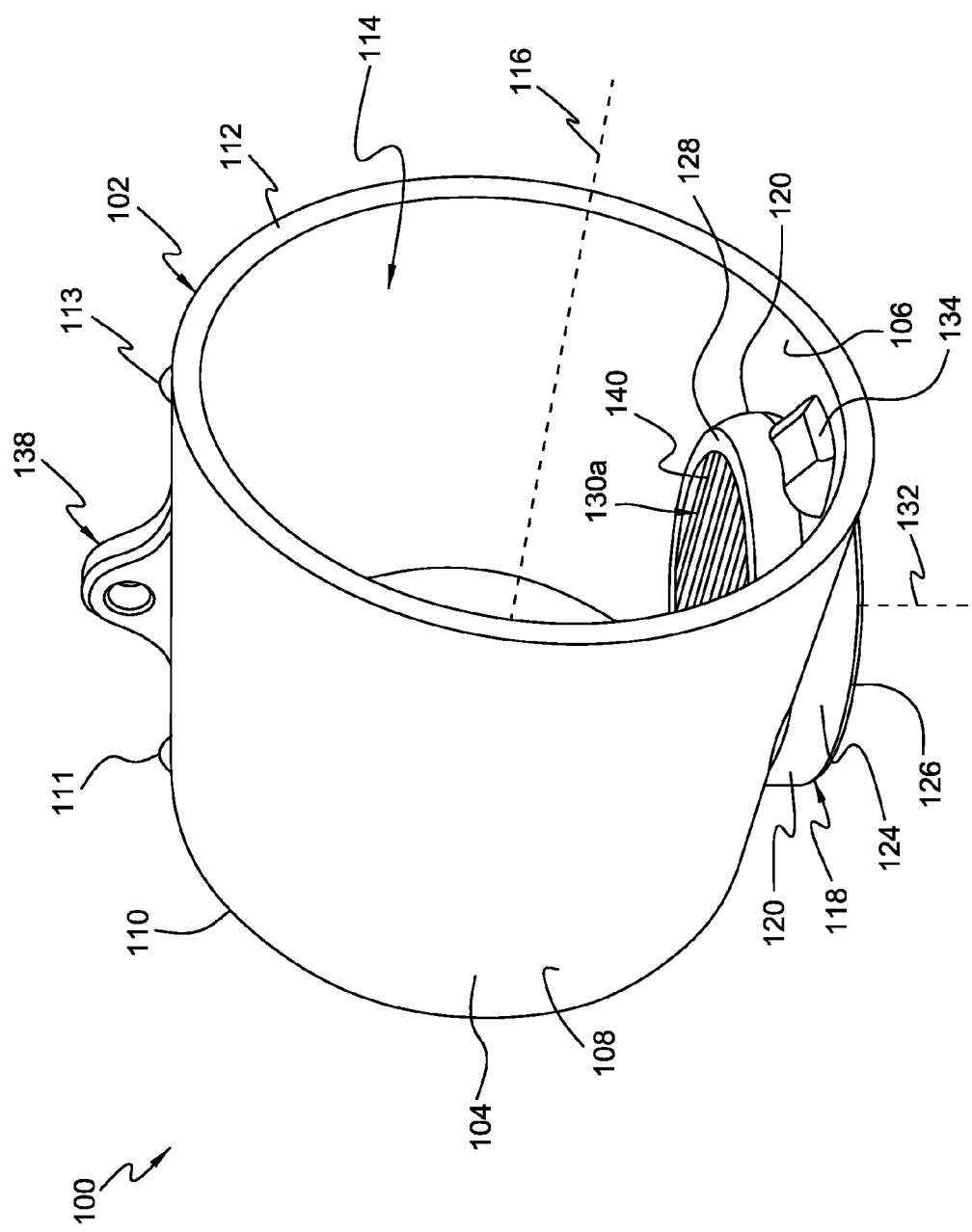
FIG. 1 is a perspective view of an airflow treatment device that is configured to treat air in an air handling system.
Figure 2:
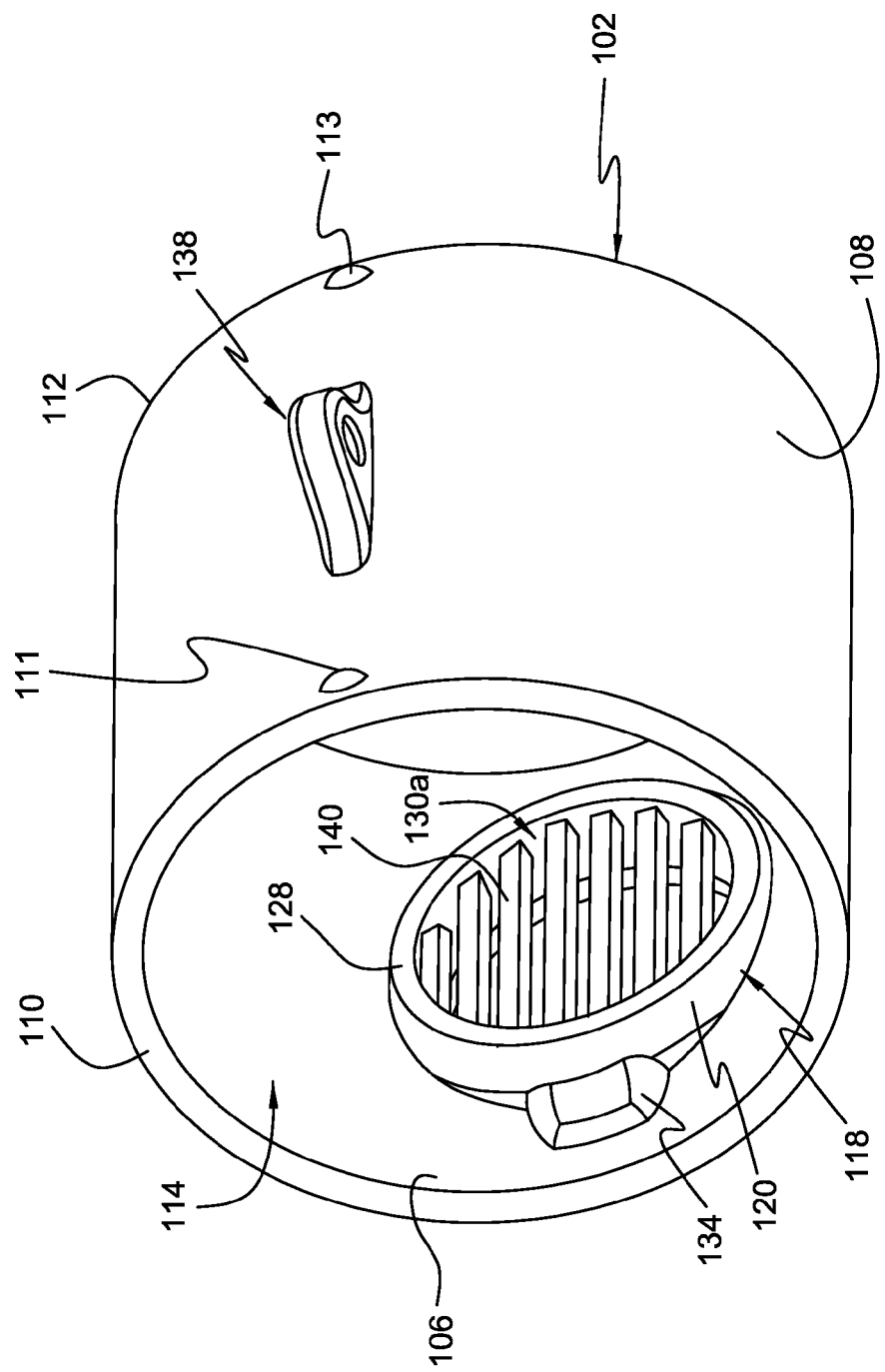
FIG. 2 is another perspective view of the airflow treatment device of FIG. 1.
Figure 3:
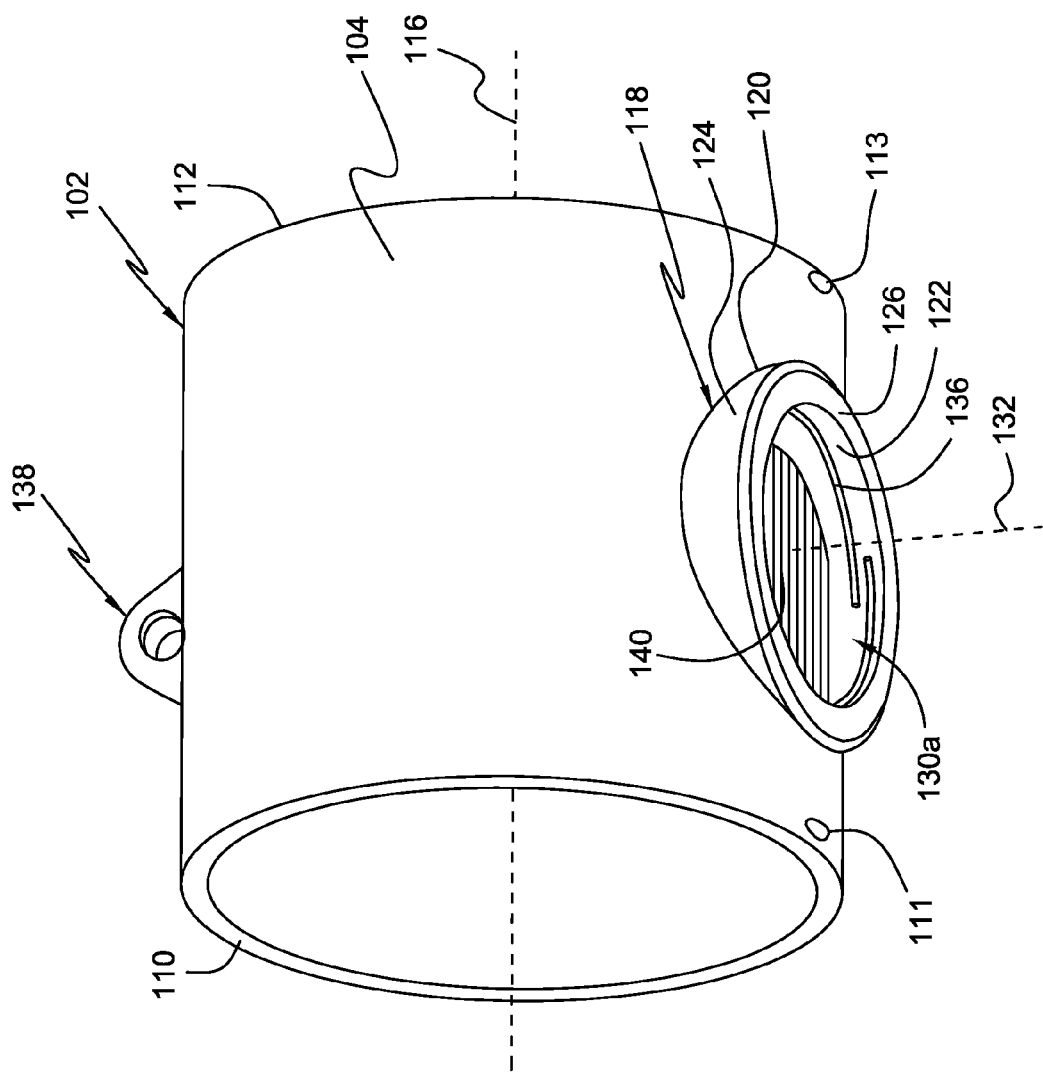
FIG. 3 is another perspective view of the airflow treatment device of FIG. 1.
Figure 4:
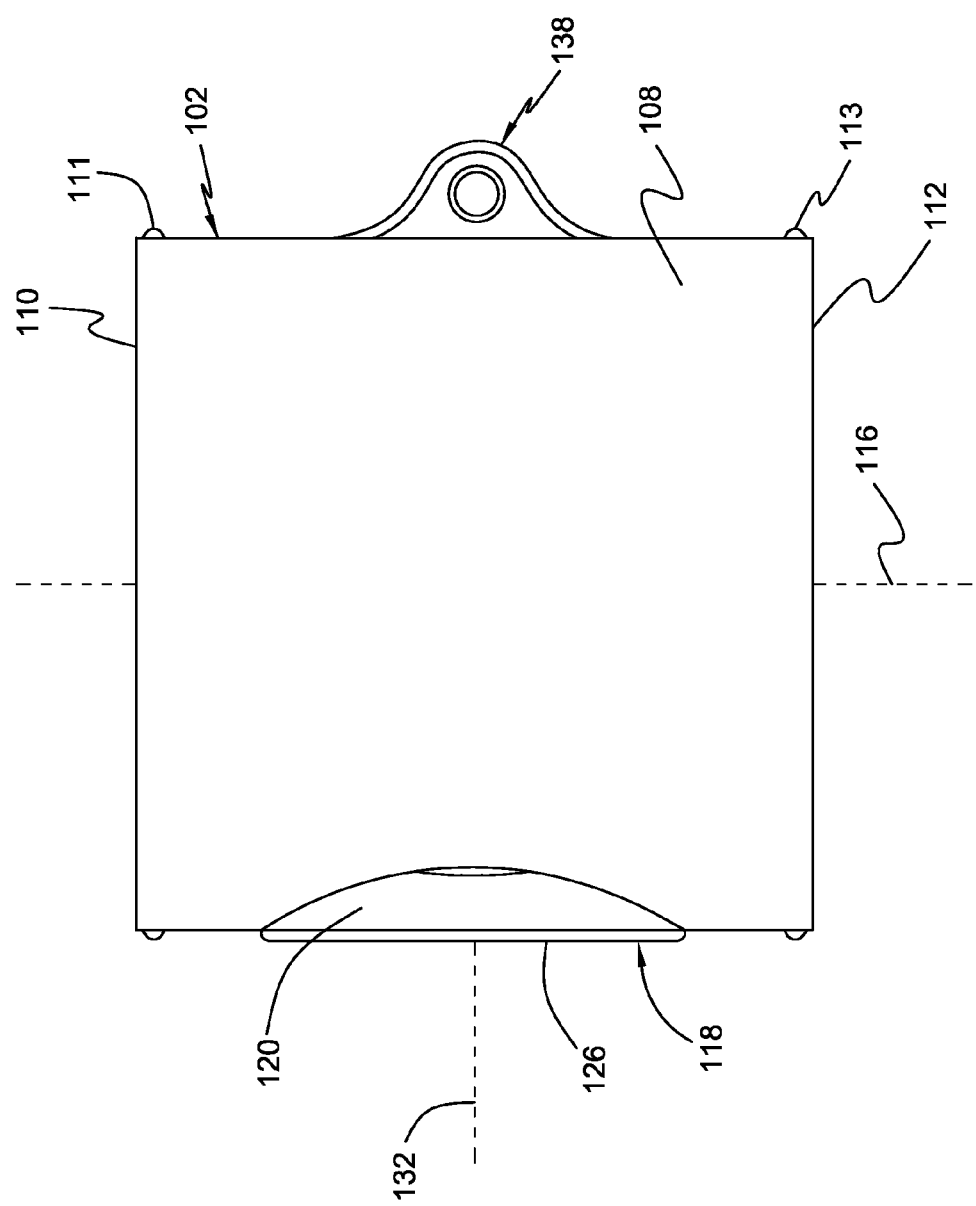
FIG. 4 is a front elevation view of the airflow treatment device of FIG. 1.
Figure 5:
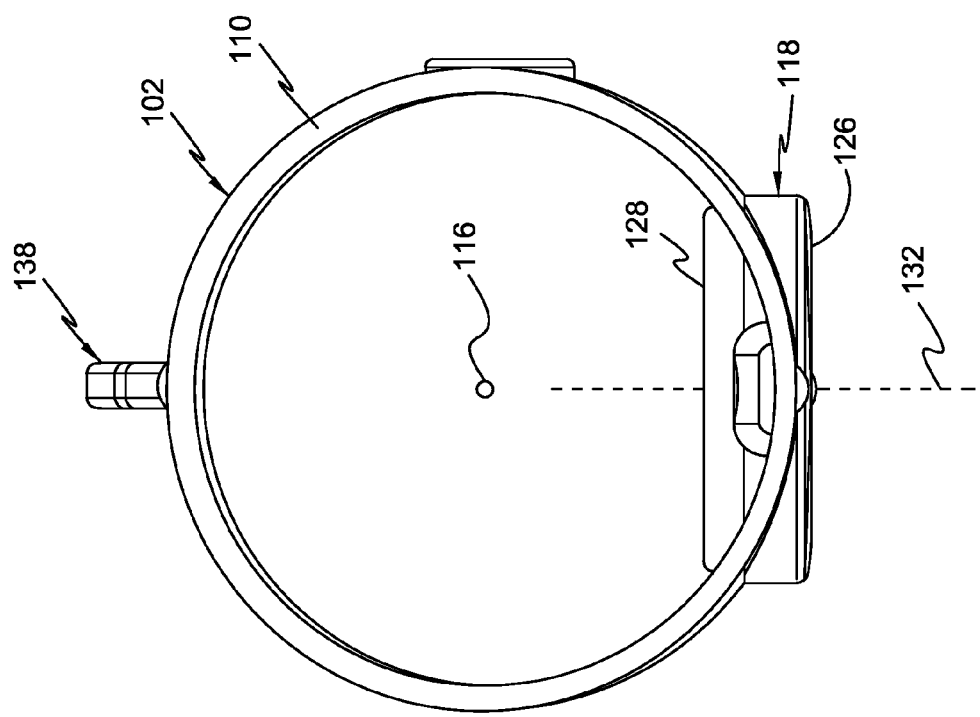
FIG. 5 is a side elevation view of the airflow treatment device of FIG. 1.
Figure 6:
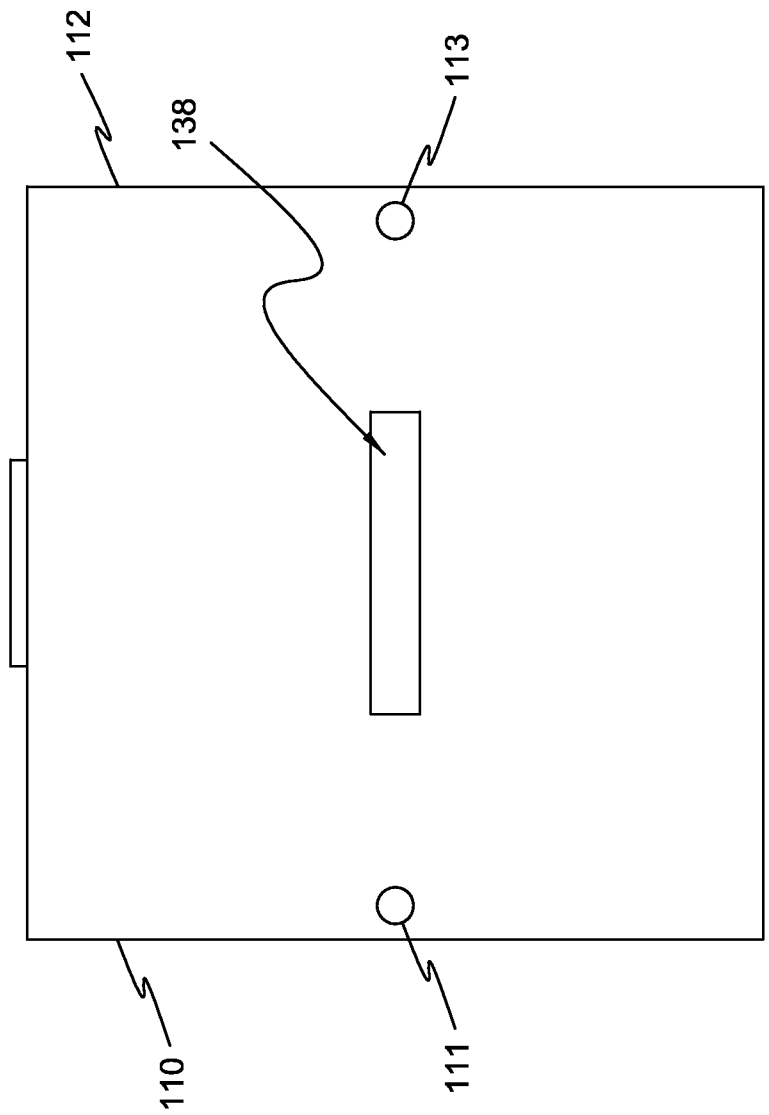
FIG. 6 is a top view of the airflow treatment device of FIG. 1.
Figure 7:
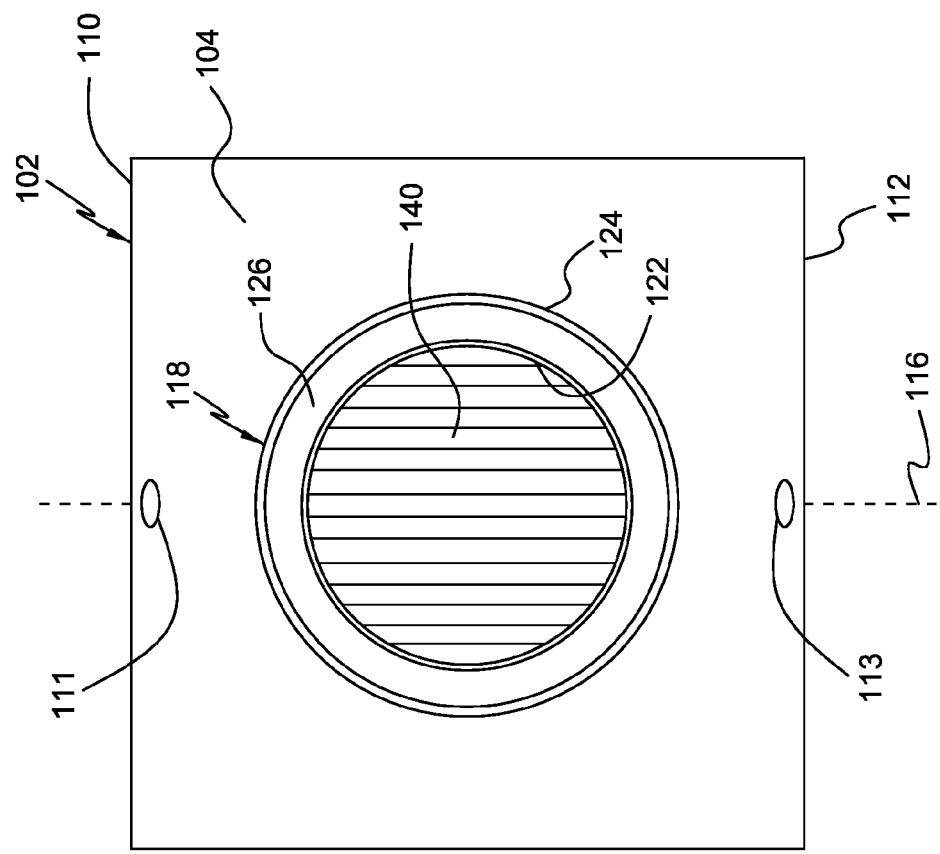
FIG. 7 is a bottom view of the airflow treatment device of FIG. 1.

FIGS. 1-7 present various views of an airflow treatment device 100 that is configured to treat air in an air handling system. As will be discussed in more detail herein, the airflow treatment apparatus or device 100 is configured to be installed inline in the ductwork of an air handling system (e.g., HVAC system) in a manner that is substantially free of obstructing the airflow through the ductwork or requiring any supplemental power to treat the airflow passing by the treatment device. The disclosed airflow treatment device can also be maintained substantially free of any interruptions, disassembly or downtime to the air handling system after initial inline installation of the disclosed airflow treatment device 100.

Broadly, the device 100 includes a first body 102 having a first wall 104 with opposite inner and outer surfaces 106, 108 and opposite first and second open free ends 110, 112. The first wall 104 defines an airflow passageway 114 through the device 100 that extends between the first and second opposite open ends 110, 112 of the first wall 104 along an airflow passageway (e.g., central) axis 116 (e.g., where the inner surface 106 of the first wall 104 generally defines and surrounds the airflow passageway 114). In this regard, the first and second opposite open ends 110, 112 may refer to both the first and second opposite open ends of the first wall 104 and first and second opposite open ends of the airflow passageway 114. The first and second open ends 110, 112 are configured to connect with (e.g., receive, be received by) respective open ends of first and second ducts or duct members (e.g., see FIGS. 8-9, discussed in more detail below) so that the airflow passageway 114 substantially seamlessly blends into the airflow passageways of the first and second ducts or duct members. While the first wall 104 is illustrated in the form of a generally tubular member having a circular cross section (e.g., a cylinder), the first wall 104 may have other cross-sectional shapes such as square, ovular, etc. (e.g., so as to generally match the cross-sectional shapes of the first and second ducts or duct members).

The device 100 also includes an arrangement for providing access to the airflow passageway 114 when the first and second open ends 110, 112 are respectively interconnected to first and second ducts or duct members in a manner that is substantially free of interrupting or blocking the airflow passageway 114 and/or requiring disconnection of the first and second ducts or duct members from the first and second open ends 110, 112 of the first body 102. For instance, the device 100 may include a second body 118 having a second wall 120 with opposite inner and outer surfaces 122, 124 and opposite first and second opposite open free ends 126, 128. The second wall 120 defines at least a first portion 130a of an air treatment passageway 130 through the first wall 104 of the device 100 that extends between the first and second open ends 126, 128 of the second wall 120 along an air treatment passageway axis 132 and that intersects the airflow passageway 114 at a position between the first and second open ends 110, 112 of the first wall 104. In this regard, the first and second opposite open ends 126, 128 may refer to both the first and second opposite open ends of the second wall 120 and first and second opposite open ends of the air treatment passageway 130.

As shown, the air treatment passageway 130 feeds substantially directly into the airflow passageway 114 to expose airflow passing through the airflow passageway 114 to one or more air treatment (e.g., odor neutralizing) substances or the like disposed within the air treatment passageway 130. To limit or reduce airflow obstruction through the airflow passageway 114, the second open end 128 of the second body 102 may extend into the airflow passageway 114 no more than about 50% of the inner diameter (or other inner maximum cross-dimension), such as no more than about 25% of the inner diameter (or other inner maximum cross-dimension). To facilitate appropriate interaction between the airflow and the air treatment substances, the second open end 128 of the second body 102 may extend into the airflow passageway 114 at least about 5% of the inner diameter, such as at least about 15%. In one arrangement, the second body 118 may be inserted partially through an aperture (not labeled) through the first wall 104 of the first body 102 and rigidly secured thereto in any appropriate manner. For instance, after insertion of the second body 118 through the first wall 104, one or more connection members 134 (e.g., welds, etc.) may be used to rigidly and non-movably secure the second body 118 to the first body 102 (e.g., such as between the outer surface 124 of the second wall 120 and the inner surface 106 of the first wall 104).

In another arrangement, the second body 118 may be in the form of a pair of opposing second body members (e.g., where the first opposing body member includes the first open end 126 and the second opposing body member includes the second open end 128) that are respectively configured to attach to each other on opposite sides of the first wall 104. As just one example, the first and second opposing body members may have respective corresponding threaded surfaces (or other respective corresponding connection members such as spring-loaded members and correspondingly shaped holes) that are configured to appropriately engage with each other. In this regard, the first and second opposing body members may be placed over the aperture through the first wall 104 adjacent the outer and inner surfaces 108, 106, respectively, and threadably secured to each other. In a further arrangement, the first and second bodies 102, 118 be part of a one-piece body that defines the airflow passageway 114 and the air treatment passageway 130. That is, the device 100 may be in the form of an integral, one-piece member that may be fabricated in any appropriate manner (e.g., blow molding, injection molding, etc.).

Figure 8:
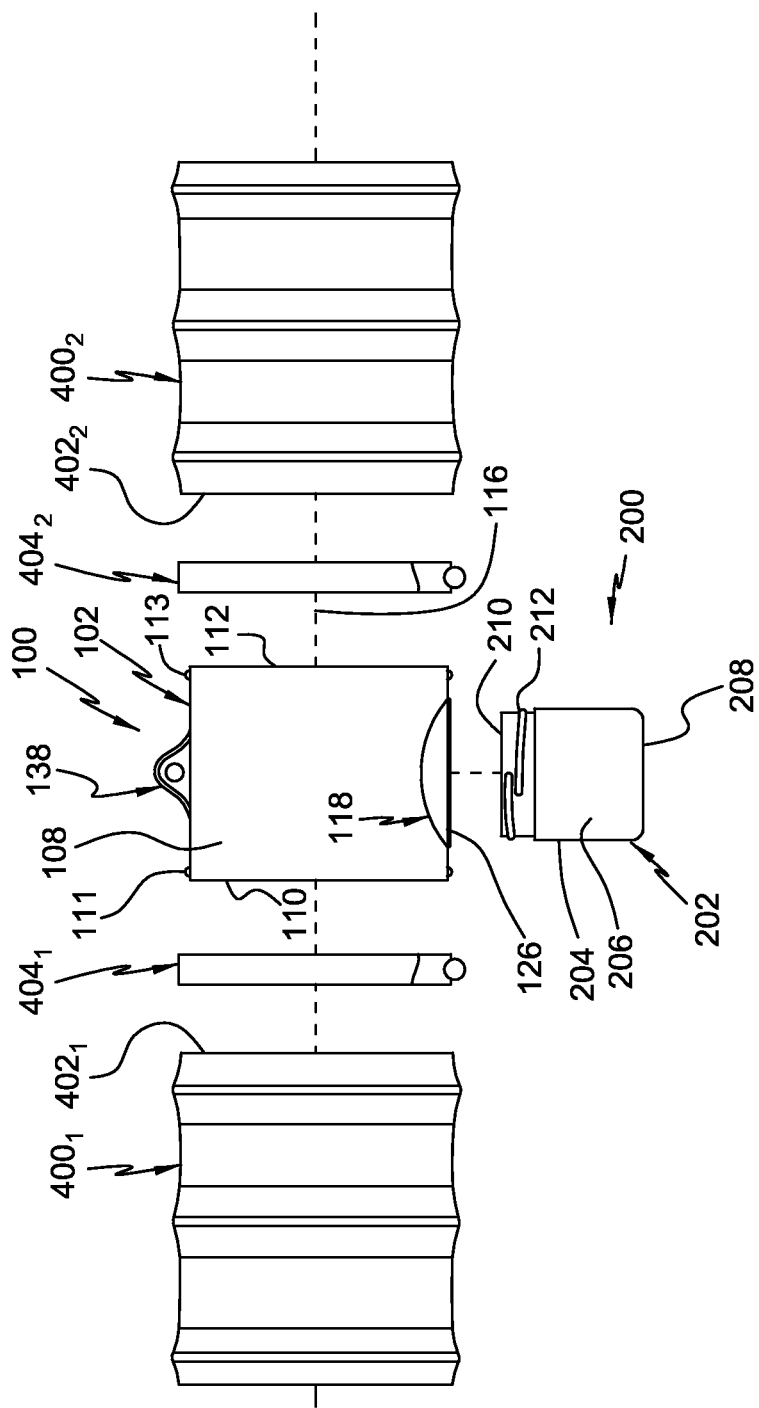
FIG. 8 is a front exploded view of the airflow treatment device of FIG. 1, an airflow treatment container, first and second duct members, and first and second securement devices for securing the first and second duct members to the airflow treatment device.
Figure 9:
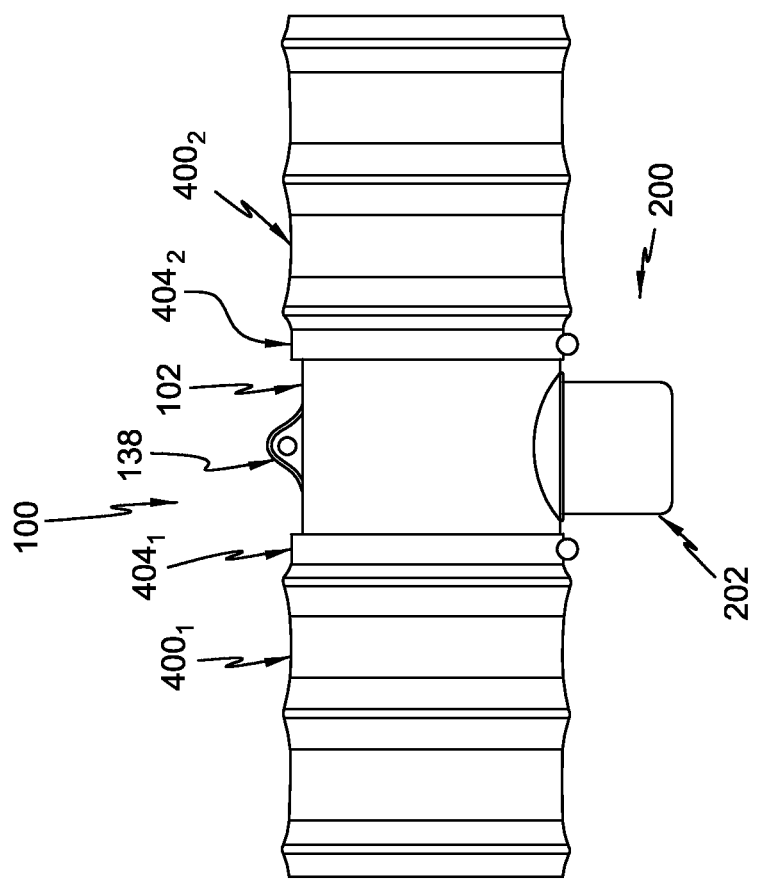
FIG. 9 is similar to FIG. 8 but with the first and second duct members being secured to the airflow treatment device with the first and second securement devices and the airflow treatment container being secured to the airflow treatment device.
Figure 14:
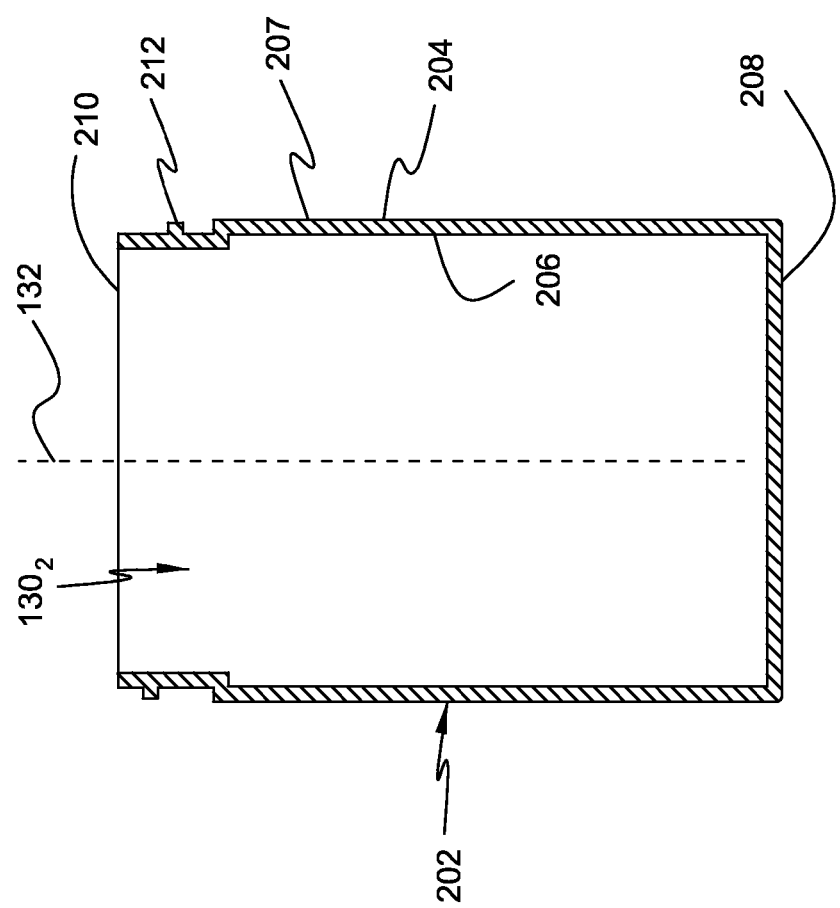
FIG. 14 is a sectional view of the airflow treatment container of FIG. 8.

In any case, the first open end 126 of the second wall 120 may be disposed outside of the airflow passageway 114 to facilitate interconnection with an air treatment container 200 (e.g., jar, bottle, glass, vial, jug, etc., see FIGS. 8, 9 and 14) having an air treatment substance therein. Stated differently, the first open end 126 may provide an opening into the air treatment passageway 130 and thus access to the airflow passageway 114 for the air treatment substance disposed in the air treatment container 200. With reference to FIGS. 8 and 14, the air treatment container 200 may include a body 202 (e.g., a "third" body) having a wall 204 (e.g., a "third" wall) with opposite inner and outer surfaces 206, 207, a closed first free end 208, and an opposite open second free end 210. The third wall 204 defines at least a second portion 130b of the air treatment passageway 130 that extends between the first and second ends 208, 210 of the third wall 204 along the air treatment axis 132 and that is configured to feed into the first portion 130a of the air treatment passageway 130 (e.g., when the second open end 210 of the air treatment container 200 is releasably secured to the first open end 126 of the second body 118).

The device 100 and the air treatment container 200 include respective first and second releasable interconnection apparatuses 136, 212 that engage to releasably secure the air treatment container 200 to the device 100 so that the second portion of the air treatment passageway 130 within the air treatment container 200 aligns with and feeds into the first portion of the air treatment passageway 130 within the second body 118 of the device 100. For instance, the first releasable interconnection apparatus 136 may be in the form of a first set of threads disposed on the inner surface 122 of the second body 118 adjacent the first open end 126 while the second releasable interconnection apparatus 212 may be in the form of a second set of threads (complimentary to the first set of threads) disposed on the outer surface 207 of the third body 202 adjacent the second open end 210. Furthermore, the second open end 210 of the third body 202 may be sized and shaped to be received through the first open end 126 and into the second body 118.

In this regard, a user may align the second open end 210 of the third body 202 with the first open end 126 of the second body 118 and then rotate the third body 202 about the air treatment axis 132 to threadingly engage the first and second sets of threads and releasably secure the air treatment container 200 to the device 100. In one arrangement, the first set of threads may be disposed on the outer surface 124 of the second body 118 while the second set of threads may be disposed on the inner surface 206 of the third body 202 adjacent the second open end 210. In this regard, the first open end 126 of the second body 118 would be received inside the second open end 210 of the third body 202. The first and second releasable interconnection apparatuses 136, 212 may also take other forms such as complimentary magnetic mechanisms, "twist and click" type mechanisms, and/or the like.

Figure 10:
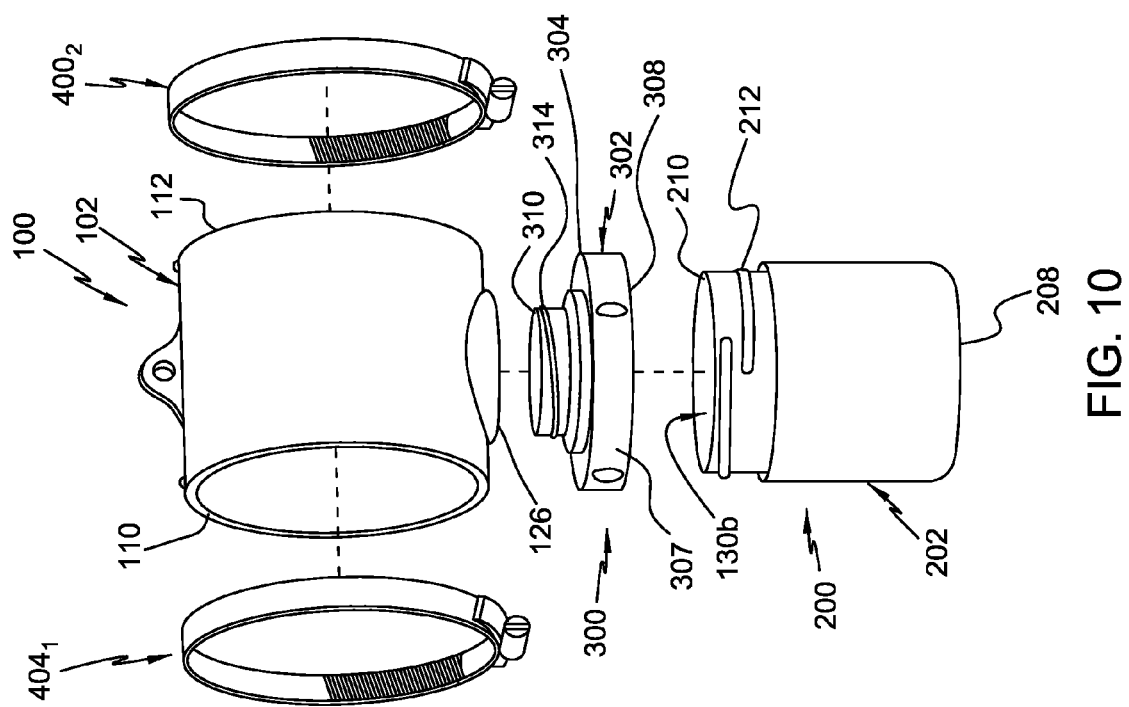
FIG. 10 is an exploded perspective view of another embodiment of the airflow treatment device, an airflow treatment container, an adapter for connecting the airflow treatment container to the airflow treatment device, and first and second securement devices for securing first and second duct members to the airflow treatment device.
Figure 11:
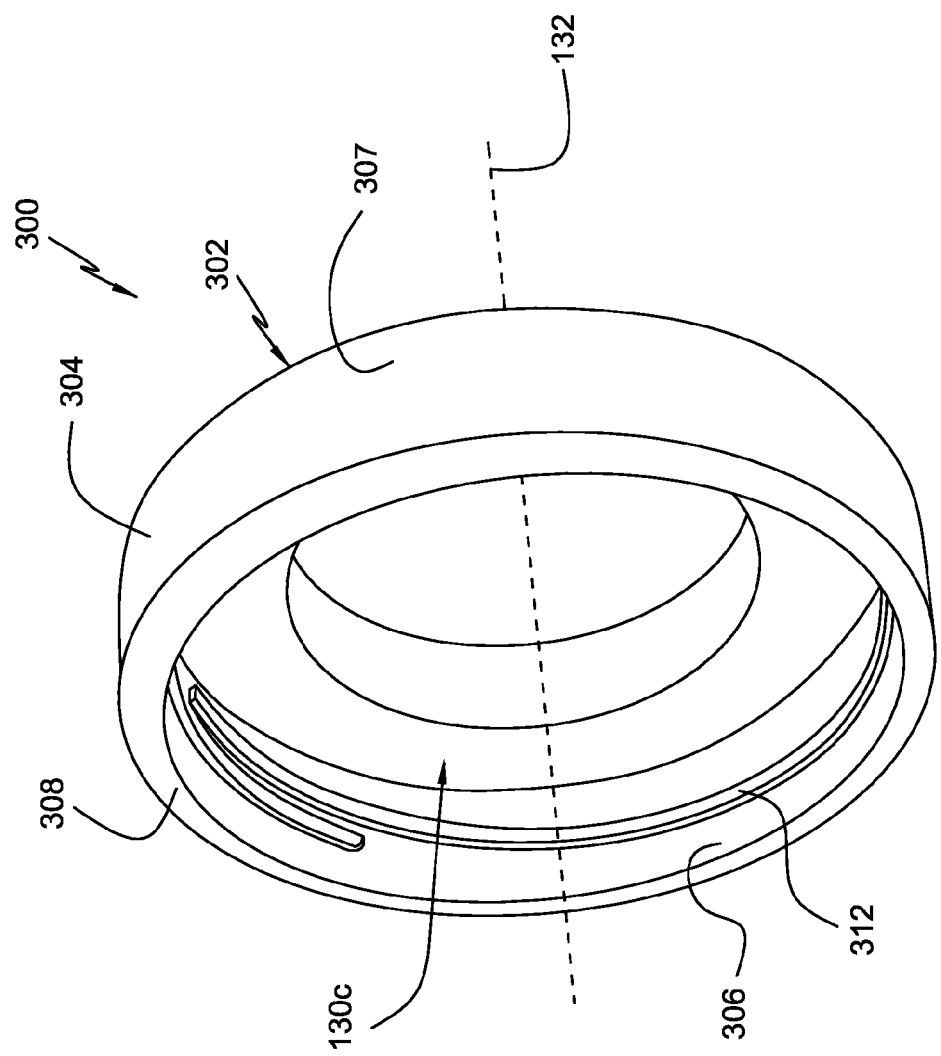
FIG. 11 is a perspective view of the adapter of FIG. 10.

In some situations, the second open end 210 of the third body 202 may not be sized and shaped to be received through the first open end 126 and into the second body 118. In this regard, a coupler or adapter 300 may be provided (see FIGS. 10-11) that is broadly configured to releasbly interconnect the air treatment container 200 to the device 100. As shown, the adapter 300 may include a body 302 (e.g., a "fourth" body) having a wall 304 (e.g., a "fourth" wall) with opposite inner and outer surfaces 306, 307 and first and second opposite open free ends 308, 310. The fourth wall 304 defines at least a third portion 130c of the air treatment passageway 130 that extends between the first and second ends 308, 310 of the third wall 304 along the air treatment axis 132 and that feeds into the first and second portions 130a, 130b of the air treatment passageway 130 (e.g., when the first and second open ends 308, 310 are respectively releasably secured to the second open end 212 of the third body 202 and the first open end 126 of the second body 118). The first open end 308 of the fourth body 302 may be sized and shaped to receive the second open end 210 of the third body 202 while the second open end 310 of the fourth body 302 may be sized to be received in the first open end 126 of the second body 118 (or vice versa).

The adapter 300 may include first and second releasable interconnection apparatuses 312, 314 that are respectively releasably interconnectable with the second releasable interconnection apparatus 212 of the third body 212 and the first releasable interconnection apparatus 136 of the second body 118. In one arrangement, the first releasable interconnection apparatus 312 may be in the form of a first set of threads that are configured to threadingly engage with the set of threads disposed adjacent the second open end 210 of the third body 302 while the second releasable interconnection apparatus 314 may be in the form of a second set of threads that are configured to threadingly engage with the set of threads disposed adjacent the first open end 126 of the second body 118. For instance, the first set of threads may be disposed on the inner surface 306 adjacent the first open end 308 of the fourth body 302 while the second set of threads may be disposed on the outer surface 307 adjacent the second open end 310 of the fourth body 302 (or vice versa). The first and second releasable interconnection apparatuses 312, 314 may also take other forms such as complimentary magnetic mechanisms, "twist and click" type mechanisms, and/or the like. The adapter 300 may take various forms, shapes and sizes to interconnect air treatment containers 200 of various forms, shapes and sizes with the device 100.

One method of installing and using the device 100 will now be described to facilitate the reader's understanding of the device 100. With initial reference to FIG. 8, a user may identify a location along the ductwork of an air handling system in which to install the device 100. For instance, the device 100 may be installed in a portion of the ductwork leading into the blower fan (e.g., on the draw or intake side). Once a location has been identified, the user may appropriately sever or cut the ductwork to obtain first and second ductwork members 400₁, 400₂. Depending upon the particular circumstances, the severing may include severing the ductwork at first and second locations to remove a section of the ductwork.

In any case, the first and second ductwork members 400₁, 400₂ may generally be in the form of hollow tubular member having respective open ends 402₁, 402₂. The open end 402₁ of the first ductwork member 400₁ may then be appropriately secured over the first open end 110 of the first body 102 and the open end 402₂ of the second ductwork member 400₂ may then be appropriately secured over the second open end 112 of the first body 102 in any appropriate manner. As just one example, first and second hose clamps 404₁, 404₂ may be initially disposed over the respective open ends 402₁, 402₂ of the first and second ductwork members 400₁, 400₂ or the first and second open ends 110, 112 of the first body 102. After the respective open ends 402₁, 402₂ of the first and second ductwork members 400₁, 400₂ have been placed over the first and second open ends 110, 112 of the first body 102, the first and second hose clamps 404₁, 404₂ may be respectively slid over the overlapping portions of the open ends 402₁, 402₂ and the first and second open ends 110, 112 and then tightened to secure the open ends 402₁, 402₂ to the body 102. See FIG. 9.

In one arrangement, the outer surface 108 of the first body 102 may include one or more retention features such as first and second retention protrusions 111, 113 (e.g., bumps, etc.) adjacent the first and second open ends 110, 112 that are configured to respectively resist removal of the first and second ductwork members 400₁, 400₂ from the first and second open ends 110, 112 of the first body 102. For instance, the open ends 402₁, 402₂ of the first and second ductwork members 400₁, 400₂ may be pulled or pushed over the first and second open ends 110, 112 of the first body 102 so as to extend at least partially past the respective first and second retention protrusions 111, 113. In one arrangement, a respective plurality of each of the first and second retention protrusions 111, 113 may be respectively disposed adjacent the first and second open ends 110, 112 of the first body 102.

In the case where the open ends 402₁, 402₂ of the first and second ductwork members 400₁, 400₂ have respective inner diameters less than outer diameters of the first and second open ends 110, 112 of the first body 102 and have sufficient levels of elasticity, the first and second ductwork members 400₁, 400₂ may be sufficiently secured to the first body 102 at this point. Additionally or alternatively, the first and second hose clamps 404₁, 404₂ may be used as discussed above. While the first and second hose clamps 404₁, 404₂ and/or first and second retention protrusions 111, 113 have been disclosed to secure the first and second ductwork members 400₁, 400₂ to the first and second open ends 110, 112 of the first body 102, other manners of securing the same are envisioned and encompassed herein.

In one arrangement, the device 100 may be appropriately hung from or otherwise secured to a fixed member (e.g., structural member of the house or building, such as a joist, etc.) at a point above the first and second ductwork members 400₁, 400₂ to limit or otherwise reduce the load placed on the first and second ductwork members 400₁, 400₂ by the device 100 (as well as by the air treatment container 200 and/or adapter 300). As just one example, the device 100 may have a first connector member 138 (e.g., hole, hook, opening, etc.) disposed on the outer surface 108 of the first body 102 that is configured to connect with or attach to a corresponding second connector member (e.g., hook, hole, etc., not shown) on a joist or other fixed member of the house or building (not shown).

In any case, the airflow passage 114 of the first body 102 substantially seamlessly feeds or blends into those of the first and second ductwork members 400₁, 400₂ (and thus the rest of the air handling system) once the open ends 402₁, 402₂ are secured over the first and second open ends 110, 112 of the first body 102. Either before or after the device 100 is secured to the first and second ductwork members (or vice versa), the air treatment container 200 including an air treatment (e.g., odor treatment or elimination) substance (e.g., liquid, solid, etc.) may be releasably secured to the second body 118 of the device 100 (as discussed previously) so that the second portion 130b of the air treatment passageway 130 (inside the air treatment container 200) aligns with and feeds into the first portion 130a of the air treatment passageway 130 (inside the second body 118), the latter of which feeds directly into the airflow passageway 114. If necessary, the adapter 300 may be used as previously discussed to interconnect the air treatment container 200 to the device 100.

Upon operation of the air handling system so that the blower fan or other device moves air through the first ductwork member $400_1$, the airflow passageway 114 of the device 100, and then the second ductwork member $400_2$ (or vice versa), the air interacts with the air treatment substance in the air treatment container 200 via the air treatment passageway 130 to neutralize or otherwise treat the air traveling through the air handling system and/or through one or more registers into one or more rooms of the home or building. In one arrangement, the second body 118 may include a screening element 140 (e.g., filter, etc.) disposed across the first portion 130a of the air treatment passageway 130 to limit particulates and/or the like in the air treatment substance from being sucked into the airflow passing through the airflow passageway 114 and into the ductwork of the air handling system. For instance, the screening element 140 may be disposed adjacent the second open end 128 of the second body 118. In one arrangement, at least a portion of the screening element 140 may extend at least a portion past the second free end 128. In other arrangements, the screening element 140 may additionally or alternatively be disposed in other locations such as across the second portion 130b of the air treatment passageway 130 adjacent the open second end 210 of the air treatment container 200, across the third portion 130c of the air treatment passageway 130 in the adapter 300, and/or the like.

Continued cycling of the air through the air handling system and the device 100 results in increased degrees of neutralizing and/or treatment of the air. The air treatment container 200 may be removed (e.g., unscrewed, unclipped, etc.) from the device 100 to recharge, replenish, etc. the air treatment substance in the air treatment container according to any appropriate schedule (e.g., every month, every six months, etc.), upon the substance dropping below a certain level, upon the substance changing colors indicating that new and/or additional substance is needed, etc. Alternatively, the air treatment container 200 may be removed from the device 100 and a new air treatment container 100 (e.g., with new air treatment substances therein) may be installed into the device 100 as discussed above. More than one device 100 and corresponding container 200 may be installed inline in a single air handling system (e.g., in each of one or more ducts of the system). In one arrangement, the device 100 and air treatment container 100 (e.g., with or without air treatment substances therein) may be supplied as or otherwise form a kit. For instance, the device 100 and air treatment container 200 may be disposed in a common packaging and supplied to retailers, sold to customers, etc. In this arrangement, the air treatment container may be releasably secured to the device 100 or not secured to the device 100 but releasably securable to the device (i.e., capable of being releasably secured to the device 100 as disclosed herein).

Figure 12:
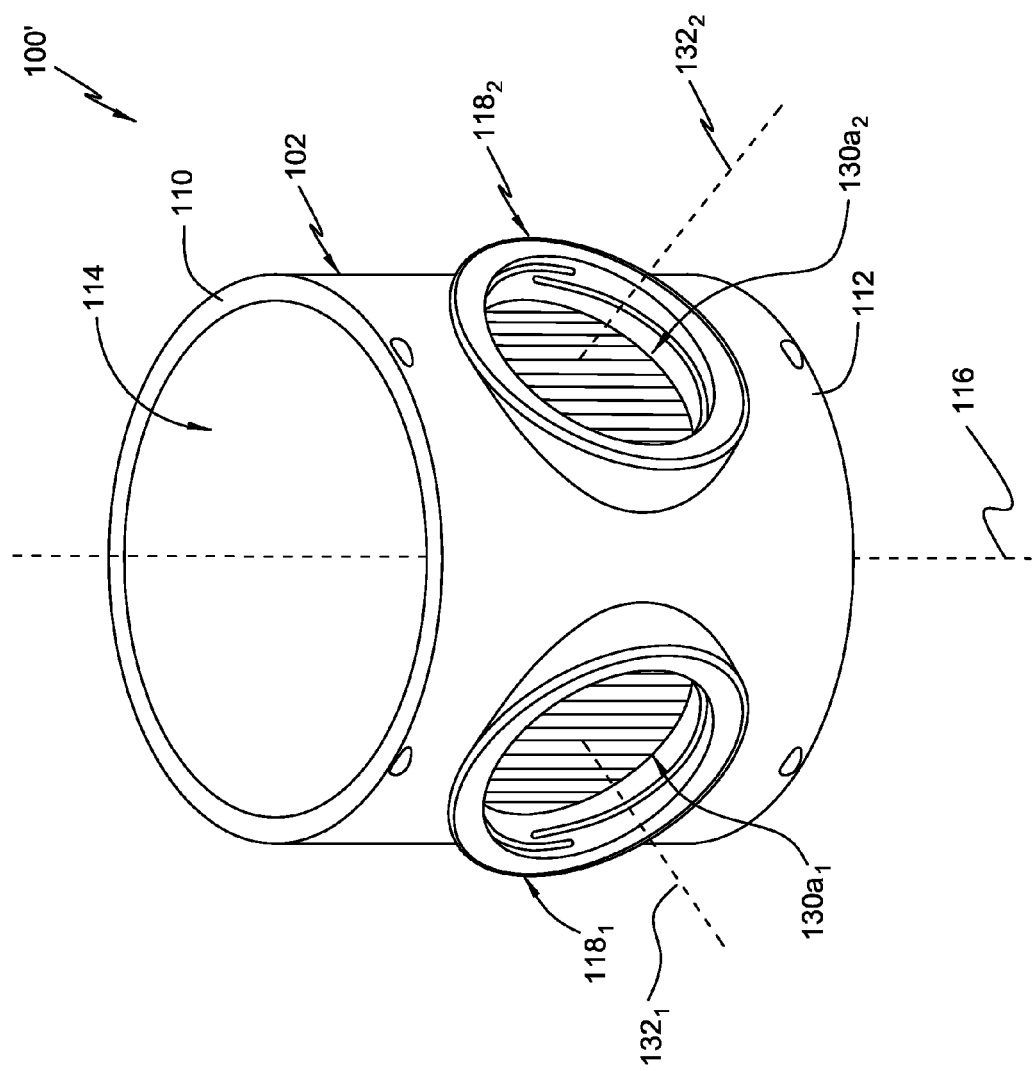
FIG. 12 is a perspective view of another embodiment of the airflow treatment device.
Figure 13:
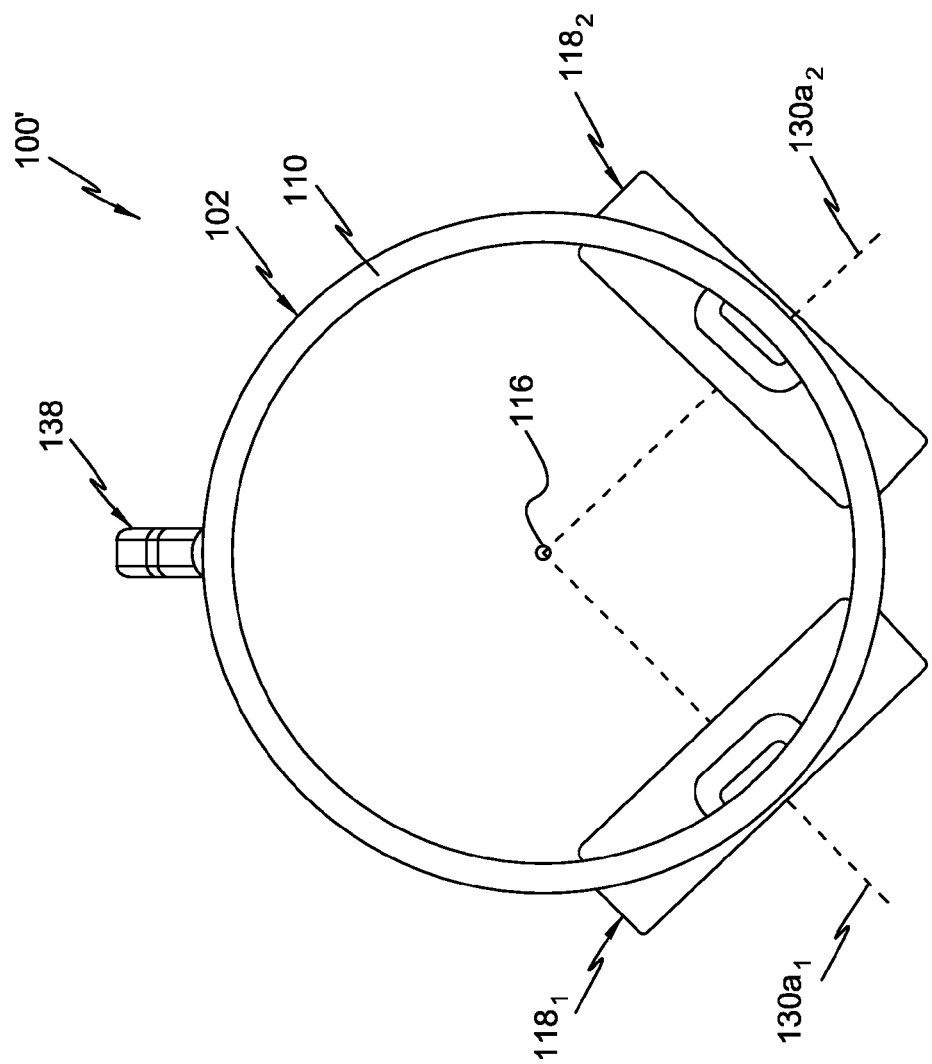
FIG. 13 is a side view of the airflow treatment device of FIG. 12.

As shown in the figures, the air treatment passageway axis 132 may in some embodiments be substantially perpendicular to the airflow passageway axis 116. In other arrangements, however, the air treatment passageway axis 132 may be other than substantially perpendicular to the airflow passageway axis 116. For instance, the air treatment passageway axis 132 may be disposed at angles greater than or less than 90° relative to the airflow passageway axis 116 (e.g., 30°, 45°, 120°, etc.). In one embodiment, a device 100 may include more than a single air treatment passageway 130 for respective interconnection to more than a single air treatment container 200. As an example, FIG. 12-13 illustrate another embodiment of the device 100' that includes a plurality of (e.g., such as first and second) second bodies $118_1$, $118_2$ that define a respective plurality of (e.g., such as first and second) air treatment passageway first portions $130a_1$, $130a_2$ along a respective plurality of (e.g., such as first and second) air treatment passageway axes $132_1$, $132_2$. For instance, each of the air treatment passageway axes $132_1$, $132_2$ may be substantially perpendicular to each other as well as to the airflow passageway axis 116 as shown in FIGS. 12-13. In one arrangement, one or both of the air treatment passageway axes $132_1$, $132_2$ may be other than perpendicular to the airflow passageway axis 116 and/or than that perpendicular to each other.

The device 100, container 200, adapter 300, ductwork members 400, etc. may be constructed of any appropriate materials (e.g. plastics, metals, composites, and/or the like) and in any appropriate manner. In one arrangement, the device 100 may be constructed out of plastic using any appropriate manufacturing process. For instance, a polyurethane mix may be procured and added to a tooling mold in the shape of the device 100 (e.g., the first and/or second bodies 102, 118) and allowed to catalyze until hardened. A similar process may be used to fabricate the adapter 300. Alternatively, metered injection molding systems and/or 3D printing technologies may be used. Still further, various metallic manufacturing processes may be used to fabricate one or more of the components. In one arrangement, the air treatment container 200 may be in the form of a glass jar (e.g., a Mason jar) or the like.

The foregoing description has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. In one arrangement, the device 100 may only include the first body 102, where the first body 102 includes a threaded aperture through the first wall 104 (e.g., at location where second body 118 is disposed in the figures) that is sized and shaped to receive the second open end 210 of the air treatment container or the second open end 310 of the adapter and that leads into the airflow passageway 114. For instance, the first and second open ends 110, 112 may include first and second openings while the threaded opening through the first wall 104 may be a third opening. In this regard, the air treatment container 200 or adapter 300 may be threaded directly into the third aperture so that the second portion 130b of the air treatment passageway becomes the first portion and thus feeds directly into the airflow passageway 114 of the first body 102.

In some arrangements, the entirety of the airflow passageway 114 and/or the air treatment passageway 130 need not necessarily respectively extend along the same straight airflow passageway axis 116 and/or air treatment passageway axis 132. Stated differently, the airflow passageway 114 and/or the air treatment passageway 130 may each follow non-straight paths between the first and second opposite open ends. For instance, in the event the device 100 was to be used in a situation where the respective open ends $402_1$, $402_2$ of the first and second ductwork members $400_1$, $400_2$ came together other than substantially collinearly as shown in FIG. 8, the first body 102 may be appropriately fabricated so that the airflow passageway 114 through the first body 102 follows a curvilinear path (e.g., a substantial U-shape), follows first and second perpendicular axes (e.g., a substantial V-shape, such as where the first axis passes through the first open end 110 and the second axis passes through the second open end 112, and where the first and second perpendicular axes intersect at a mid-point of the first body 102), etc. As another example, it is not necessary that the air treatment passageway 130 follows a completely straight path from the first closed end 208 of the air treatment container 200 and the second open end of the second body 118.

In one embodiment, a cap may be provided with the device (e.g., in a kit) for use in closing or otherwise sealing off access to the airflow passageway 114 via the second body 118 or otherwise through the first wall 104 of the first body 102. For instance, the cap may have a closed head portion and a threaded portion protruding from the head portion that is configured to be inserted into the second body 102 and threadingly engage with the set of threads of the second body 102; this may be advantageous to use when the air treatment container 200 has been removed from the device 100 for any appropriate reason to limit airflow leakage from the device 100.

It is also to be understood that the various components disclosed herein have not necessarily been drawn to scale. Also, many components have been labeled herein as "first," "second," "third," etc. merely to assist the reader in understanding the relationships between the various components. One or more various combinations of the above discussed arrangements and embodiments are also envisioned. While this disclosure contains many specifics, these should not be construed as limitations on the scope of the disclosure or of what may be claimed, but rather as descriptions of features specific to particular embodiments of the disclosure. Furthermore, certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A kit for use in treating airflow in ductwork, comprising: an airflow treatment device, including:
   a first body including a first wall having inner and outer surfaces, wherein the inner surface defines an airflow passageway, and wherein the first wall includes first and second opposite open ends, and wherein the airflow passageway extends between the first and second opposite open ends of the first wall; and
   a second body including a second wall that defines a first portion of an air treatment passageway that intersects the airflow passageway, wherein the second wall includes first and second opposite open ends, wherein the first portion of the air treatment passageway extends between the first and second opposite open ends of the second wall, wherein the first open end of the second wall is disposed outside of the airflow passageway, wherein the second open end of the second wall extends into the airflow passageway by an amount equal to at least 5% of an inner maximum cross-dimension of the airflow passageway and not more than 50% of the inner maximum cross-dimension of the airflow passageway;
   an air treatment container that is one of releaseably securable or releasably secured to the first open end of the second wall, wherein the air treatment container includes a third body having a third wall that defines a second portion of the air treatment passageway that feeds into the first portion of the air treatment passageway, wherein the third wall includes a closed first end and an opposite open second end, and wherein the second portion of the air treatment passageway extends between the closed first end and the opposite open second end of the third wall; and
   an adapter that releasably secures the air treatment container to the second body, wherein the adapter includes a fourth body having a fourth wall that defines a third portion of the air treatment passageway that intersects the first and second portions of the air treatment passageway, wherein the fourth wall includes first and second opposite open ends, wherein the third portion of the air treatment passageway extends between the first and second opposite open ends.

2. The kit of claim 1, wherein the airflow treatment device includes a first releasable interconnection apparatus and wherein the air treatment container includes a second releasable interconnection apparatus that is complimentary to the first releasable interconnection apparatus.

3. The kit of claim 2, wherein the first releasable interconnection apparatus is disposed on one of the inside or the outside of the second wall and wherein the second releasable interconnection apparatus is disposed on the other of the inside or the outside of the third wall.

4. The kit of claim 1, wherein the fourth body includes a first releasable interconnection apparatus that is releasably interconnectable with the third body, and a second releasable interconnection apparatus that is releasably interconnectable with the second body.

5. The kit of claim 4, wherein the first releasable interconnection apparatus is disposed on one of the inside or the outside of the fourth wall and wherein the second releasable interconnection apparatus is disposed on the other of the inside or the outside of the fourth wall.

6. The kit of claim 1, wherein the airflow passageway includes an airflow passageway axis extending between the first and second opposite open ends of the first wall, wherein the air treatment passageway includes an air treatment passageway axis that extends between and through the first closed end and the opposite open second end of the air treatment container and also extends between and through the first and second opposite open ends of the second wall, and wherein the airflow passageway axis is perpendicular to the air treatment passageway axis.

7. The kit of claim 1, wherein the air treatment container includes at least one air treatment substance therein, and wherein the at least one air treatment substance includes at least one essential oil.

8. The kit of claim 1, wherein the first and second bodies comprise a single piece of material.

9. A system, comprising:
   the kit of claim 1;
   an open end of a first duct secured over the first open end of the first body; and
   an open end of a second duct secured over the second open end of the first body, wherein the airflow passageway is defined through the first duct, the first body, and the second duct.

10. The system of claim 9, wherein the airflow passageway is in communication with at least one blower fan that is configured to generate the airflow.

\* \* \* \* \*